(12) United States Patent
Haight et al.

(10) Patent No.: US 7,228,160 B2
(45) Date of Patent: Jun. 5, 2007

(54) SYSTEM, APPARATUS AND METHOD FOR INFERRING GLUCOSE LEVELS WITHIN THE PERITONEUM WITH IMPLANTABLE SENSORS

(75) Inventors: LeVoy Golden Haight, West Jordon, UT (US); Kevin W. Gordon, American Fork, UT (US); James L. Sorenson, Salt Lake City, UT (US)

(73) Assignee: Sorenson Medical, Inc., Salt Lake City, UT (US)

( * ) Notice: Subject to any disclaimer, the term of this patent is extended or adjusted under 35 U.S.C. 154(b) by 477 days.

(21) Appl. No.: 10/703,152

(22) Filed: Nov. 6, 2003

(65) Prior Publication Data

US 2004/0152187 A1 Aug. 5, 2004

Related U.S. Application Data

(60) Provisional application No. 60/426,266, filed on Nov. 13, 2002.

(51) Int. Cl.
*A61B 5/00* (2006.01)
(52) U.S. Cl. ............ 600/316; 600/317; 600/322; 600/341
(58) Field of Classification Search ............ 600/316, 600/317, 323, 325, 341, 342, 343
See application file for complete search history.

(56) References Cited

U.S. PATENT DOCUMENTS

| | | | |
|---|---|---|---|
| 4,657,736 A | | 4/1987 | Marsoner et al. |
| 5,030,420 A | | 7/1991 | Bacon et al. |
| 5,462,880 A | * | 10/1995 | Kane et al. .................. 436/138 |
| 5,569,186 A | * | 10/1996 | Lord et al. .................... 604/67 |
| 5,605,152 A | * | 2/1997 | Slate et al. .................. 600/316 |
| 5,957,890 A | * | 9/1999 | Mann et al. ................. 604/131 |
| 6,664,111 B2 | * | 12/2003 | Bentsen et al. ............... 436/68 |
| 2002/0016534 A1 | * | 2/2002 | Trepagnier et al. ......... 600/316 |

* cited by examiner

*Primary Examiner*—Eric Winakur
*Assistant Examiner*—Etsub Berhanu
(74) *Attorney, Agent, or Firm*—TraskBritt

(57) ABSTRACT

A glucose sensor assembly useful in patient systems includes an oxygen sensor from which glucose levels in the vicinity of the peritoneal cavity may be inferred. The sensor assembly may be associated with electronics, such as any or all of a DC power supply, an LED source of blue light, a photoreceptor for red light, a CPU, and transceiver, by a direct percutaneous connection. Alternatively they may be associated transdermally with the sensor and some of the electronics being located subdurally. Insulin infusion means are contemplated to respond manually or mechanically to information from the sensors through the CPU. Mechanical response may be automatic. Infusion means may be located subdurally. It is contemplated that the present invention enable revitalization or replacement of fluorescing compounds and glucose oxidase within the sensor assembly.

36 Claims, 2 Drawing Sheets

SYSTEM, APPARATUS AND METHOD FOR INFERRING GLUCOSE LEVELS WITHIN THE PERITONEUM WITH IMPLANTABLE SENSORS

CROSS-REFERENCE TO RELATED APPLICATION

This application claims the benefit of U.S. Provisional Application No. 60/426,266 filed Nov. 13, 2002, the disclosure of which is hereby incorporated in its entirety by this reference.

BACKGROUND OF THE INVENTION

1. Field

This invention relates generally to glucose measurement for ongoing diabetes management. It provides a particularly useful application for implanting bioluminescent oxygen sensors within the peritoneum from which to infer glucose levels therein.

2. State of the Art

Heretofore treatment and management of diabetes has been undertaken through many and varied techniques. The approach predominantly used involves periodic pricks of the skin with a needle whereby a blood sample is obtained and tested directly to provide information about blood glucose levels. This information is then utilized as a basis from which to approximate a physiological equilibrium within the patient.

While such a direct measurement of glucose levels in blood samples from diabetes patients provides reasonably useful information about insulin levels at a given point in time, the dynamic nature of blood sugar physiology and the complexity of factors influencing blood sugar levels renders such information inadequate. Blood samples have characteristically been drawn from extremities of the body with blood sugar levels delayed from those that would normally trigger the body's more accurate natural production of insulin near the liver and kidneys in a non-diabetic patient. The glucose level in the peritoneal fluid more closely approximates the glucose level in the blood within the portal vein (which feeds the liver and kidneys), with a reduced lag time as compared to the glucose levels in the extremities such as the arms, legs and interstitial fluid. Similarly, the variables of patient food selection and amount, physical activity, insulin dosage, regimen, and protocol for a diabetes medical patient each have a dynamic impact on physiological balance within the patient's body that can change dramatically over a short period of time. If the net result of changes in these variables and dynamics results in a disequilibrium expressed as too much glucose ("hyperglycemia"), then more insulin is required, whereas too little glucose ("hypoglycemia") requires immediate intervention to raise the glucose levels. A deleterious impact on physiology follows either such disequilibrium.

Hyperglycemia is the source of most of the long-term consequences of diabetes, such as blindness, nerve degeneration, and kidney failure. Hypoglycemia, or insulin shock, on the other hand poses the more serious short-term danger. Insulin shock can occur at any time of the day or night and can cause the patient to lose consciousness, necessitating frequent monitoring of blood glucose levels that renders the skin-prick approach impractical, particularly with young children. Even diligent patients who perform finger-sticking procedures many times each day achieve only a poor approximation of continuous monitoring. Accordingly, extensive attention has been given to the development of improved means of monitoring patient glucose levels for treatment of diabetes.

Many efforts to continuously monitor glucose levels have involved implantable electrochemical biosensors. These amperometric sensors utilize an immobilized form of the enzyme glucose oxidase to catalyze the oxidation of glucose to gluconic acid and hydrogen peroxide. Such sensors may be used to measure hydrogen peroxide resulting from the enzymatic reaction. More typically, these biosensors measure oxygen consumption.

An example of the latter, oxygen consumption, paradigm may be found in a sensor developed by David Gough and his colleagues at the Department of Bioengineering of the University of California-San Diego. This approach allows glucose and oxygen to diffuse into the enzyme-containing portion of the sensor on one side while oxygen alone diffuses through an oxygen electrode on the other side to provide contrasting information about the background concentration of oxygen.

To provide continuous measurement, biosensors are placed within the body. One method of placement is percutaneously with an indwelling needle and an attached external wire associated with a readout device. A risk of infection is associated with percutaneous biosensors. Another disadvantage of prior art percutaneously-placed biosensors is the need for recalibration to blood glucose values at least once daily and possibly more often.

Alternatively, the sensors, transmitter and battery of prior art devices have been totally implanted in the body and transmit radio signals to an external receiver. Disadvantageously, the body responds to the implant as an insult. To protect itself against a perceived invader, the body experiences a foreign body reaction by encapsulating the implant with protein, shortening the life of the total implant and adversely affecting the accuracy of information provided. Cell and proteinacious encapsulation from a foreign body reaction typically results in reduced performance from these implanted biosensors. The size of the total implant is also regarded as a problem. Further, studies of such intravascular implants portend a risk of clotting.

Studies at the University of New Mexico headed by Dr. Ebtisam Wilkins suggest that the life of sensors can be extended by periodic infusion of fresh glucose oxidase immobilized to powdered graphite in a suspension that is then pumped into a thin channel between a membrane contacting the tissues and the electrode surface, thus flushing the spent enzyme. Such periodic infusions are susceptible to all of the disadvantages attendant to invasive procedures.

Material prior art further includes U.S. Pat. No. 4,657,736 to Marsoner, et al. entitled "Sensor element for determining the oxygen content and a method of preparing the same;" and U.S. Pat. No. 5,030,420 to Bacon, et al. entitled "Apparatus for oxygen determination." Marsoner teaches use of a sensor containing any of various fluorescent indicator substances solubilized in generally homogeneous distribution throughout a polymerized silicone polymer carrier material. Such fluorescent indicator substances tend to be toxic to a patient or other biological hosts. Disadvantageously, when such fluorescent indicator substances are dissolved homogeneously throughout a carrier, a greater exposure of the patient or other biological host to the toxic fluorescent substances is likely to result. Bacon similarly teaches fluorescing complexes immobilized and isolated throughout an insoluble matrix such as light-transmissive silicone rubber.

There remains a need for a sensor apparatus wherein a fluorescing indicator substance is encapsulated within a surrounding barrier rather than dispersed homogeneously throughout such barrier. The need would be beneficially addressed at least in part by provision of an implantable sensor wherein an indicator substance capable of fluorescing is encapsulated within an oxygen permeable silicone polymer carrier material.

A need exists for a sensor suitable for location in the vicinity of the peritoneum as a part of a system and method for inferring glucose levels within the peritoneum. This need would be addressed by location of a sensor within the peritoneum, whether other portions of the system associated with the sensor, such as light source, photoreceptors, batteries and CPU, are located outside of the body or embedded within the body. Such a sensor would beneficially be susceptible to periodic revitalization, preferably less invasively or noninvasively.

A further need exists for a method of infusing insulin into the vicinity of the peritoneum in response to inferences of glucose levels within the peritoneum suggestive of the onset of a hyperglycemic condition. Such a means would desirably allow for the subject patient to directly respond by affecting the timing and nature of such insulin infusion relative to prevailing conditions or would alternatively allow for a third party or automated response that may in one alternative embodiment be remotely actuated.

SUMMARY OF THE INVENTION

In one preferred embodiment, the invention may be arranged to form a system for measuring and monitoring glucose concentration in the peritoneum of an animal or human body. The inventive system includes a first fiber optic structure. This first fiber optic structure includes a first optical fiber having a first proximal end and a first distal end. The first distal end is connected to a first optically-active sensor, or optrode. The first sensor typically includes luminescent material encapsulated by an oxygen permeable polymer barrier. Such an embodiment generally includes a second fiber optic structure, potentially having a second optical fiber. The second optical fiber, if present, has a second proximal end and a second distal end. The second distal end is generally connected to a second sensor. The second sensor desirably is located substantially proximal to the first sensor, but not so close as to interfere with the local chemistry in the vicinity of the first sensor.

The second sensor also typically includes luminescent material encapsulated by an oxygen permeable polymer barrier and further desirably includes an agent or substance, such as glucose oxidase, operable to change local fluid chemistry in the vicinity of the second sensor. The glucose oxidase can be carried in (or by) any operable structure, such as a pocket. Alternatively, the active agent may be applied as a coating. The glucose oxidase is desirably arranged adjacent to both the second sensor and the polymer barrier.

Typically, an instrument is provided and arranged to measure a difference, in some measurable quantity, between each sensor as a way to infer glucose levels in the patient's body. As an example measurement, a shift in light wavelength, or an intensity of fluorescence, can be measured and used to infer glucose levels in a patient. One arrangement operable to make such a measurement includes a source of blue light, associated with the first and second proximal ends. The light source can be structured and arranged to transmit blue light directed from the first and second proximal ends toward the luminescent material of the first and second sensors, respectively. A device for measuring a phase shift due to luminescence generated in the luminescent material of the first sensor and the second sensor upon (a) absorption of blue light, (b) fluorescing and (c) reemission of red light are included in this invention.

The invention may also include structure, such as a cannula or catheter, for placing the first sensor and the second sensor within the peritoneal cavity. Alternative surgical techniques for effecting such placement are also within contemplation. An advantage of intraperitoneal placement of the sensing apparatus is that foreign body reaction to the sensor is diminished compared to subcutaneous, or vascular implantation.

The blue light may comprise an electromagnetic current in a range of wavelengths less than 500 nanometers. The red light may comprise an electromagnetic current in a range of wavelengths in excess of 600 nanometers. Each optical fiber may comprise a diameter in the range of 50 microns up to 600 microns. The luminescent material may comprise ruthenium (II) complex or an aromatic hydrocarbon. The aromatic hydrocarbon may include carbazole, acridone, fluoranthene, 9,10-diphenylanthracene, phrysene, benz(a)anthracene, tetracene, pyrene, dibenz(ah)anthracene, perylene, benzo(ghi)perylene, coronene, anthanthrene, decacyclene, 1-aminoanthracene, 2-aminoanthracene or 1-aminopyrene.

The invention may alternatively be embodied as an apparatus for measuring glucose concentration utilizing a first sensor wherein luminescent material encapsulated by a first oxygen permeable polymer barrier is located proximal a distal end of a first optical fiber; a second sensor wherein luminescent material and glucose oxidase adjacent each other and together encapsulated by a second oxygen permeable polymer barrier are located proximal a distal end of a second optical fiber in near proximity to the first sensor for placement of the first and second sensors within a peritoneal cavity of a medical patient to infer glucose levels therein; a source of blue light, emissions of which transmitted through the distal ends of the first and second optical fibers are capable of fluorescing within the luminescent material of both the first and second sensors and of being reemitted in the form of red light from both the first and second sensors; a photoreceptor structured and arranged to receive the reemitted red light from both the first and second sensors, the photoreceptor being in communication with a processor capable of comparing the information transmitted through the photoreceptor from the respective first and second sensors.

This embodiment may further comprise a direct current power supply which may be located outside the body and which may be structured and arranged to excite the source of blue light. The photoreceptor may likewise be located outside of the body. The source of blue light and the photo-receptor may alternatively both be located outside of the body. A cannula with which bodily tissues surrounding the peritoneal cavity may at a selected site be separated with minimal severance of the tissues upon insertion of the cannula through the tissues, whereby a passage may be opened for placement of the sensors within the peritoneal cavity. The passage may further be utilized for placement of the source of blue light. The passage may further be utilized for placement of one or more photoreceptors, or optrodes.

The present invention may further be embodied as a method of measuring glucose concentration, in which a first sensor is provided wherein luminescent material encapsulated by a first oxygen permeable polymer barrier is located proximal a distal end of a first optical fiber; a second sensor is provided wherein luminescent material and glucose oxidase adjacent each other and together encapsulated by a second oxygen permeable polymer barrier are located proximal a distal end of a second optical fiber in near proximity to the first sensor for placement of both sensors in the vicinity of the peritoneal cavity of a medical patient; a source of blue light if provided, emissions of which transmitted through the distal ends of the first and second optical fibers are capable of fluorescing within the luminescent material of both the first and second sensors and of being reemitted in the form of red light from both the first and second sensors; a photoreceptor is provided which is structured and arranged to receive the reemitted red light from both the first and second sensors, the photoreceptor being in communication with a processor capable of comparing information transmitted through the photoreceptor from the respective first and second sensors; a cannula may be provided, comprising an axial lumen and a leading end susceptible to insertion through the abdominal wall of the patient; the leading end typically adapted to be inserted into the vicinity of the peritoneal cavity of the patient; and both the first and second sensors can be inserted through the lumen and into the vicinity of the peritoneal cavity.

According to this method, a direct current power supply may be provided which may be located outside the body and which may be structured and arranged to be capable of exciting the source of blue light. The photoreceptor may be located outside of the body. The source of blue light and the photoreceptor may be located outside of the body. The cannula upon insertion may be structured and arranged to be capable of separating tissues comprising the abdominal wall with minimal severance of such tissues. A catheter assembly may be provided whereby therapeutic fluids may be infused into the peritoneal cavity. Such catheter assembly may comprise an in-line filter. The filter may be structured and arranged to filter both air and impurities, including particulate matter and microorganisms harmful to the peritoneal cavity. The therapeutic fluids may be infused in response to direction from the processor based upon the information. Therapeutic fluids may be infused mechanically. This mechanical infusion may be automatic or manual. It is contemplated that the mechanical infusion may further be remotely actuated. The catheter assembly may be structured and arranged for disconnection of a proximal portion of the catheter at a location proximal the filter in preparation for attachment of successive replacement catheter proximal portions. The first and second sensors may be replaced periodically.

An alternative preferred embodiment may further comprise an auxiliary lumen structured and arranged to be capable of being placed in communication with the glucose oxidase, whereby the glucose oxidase upon becoming degraded from exposure to oxygen and glucose within the peritoneum may be replaced with upgraded or new glucose oxidase. The glucose oxidase of one or more sensors therefore may be replaced by upgraded or new glucose oxidase.

Such an embodiment may further comprise an auxiliary catheter lumen in communication with the luminescent material, whereby the luminescent material upon becoming degraded through repeated fluorescing may be replaced with upgraded or new luminescent material. Upgraded or new luminescent material may replace the luminescent material of one or more sensors.

A further additional preferred method for measuring glucose concentration includes providing a first sensor wherein luminescent material encapsulated by a first oxygen permeable polymer barrier is located proximal a distal end of a first optical fiber; providing a second sensor wherein luminescent material and glucose oxidase adjacent each other and together encapsulated by a second oxygen permeable polymer barrier are located proximal a distal end of a second optical fiber in near proximity to the first sensor for placement of the sensors in the vicinity of the peritoneal cavity of a medical patient; providing a source of blue light, emissions of which transmitted through the distal ends of the first and second optical fibers are capable of fluorescing within the luminescent material of both the first and second sensors and of being reemitted in the form of red light from both the first and second sensors; providing a photoreceptor structured and arranged to receive the reemitted red light from both the first and second sensors, the photoreceptor being in communication with a processor capable of comparing information transmitted through the photoreceptor from the respective first and second sensors; and placing both of the first and second sensors in the vicinity of the peritoneal cavity.

The placement of the first and second sensors in the vicinity of the peritoneal cavity may be accomplished by providing a cannula, comprising an axial lumen and a leading end susceptible to insertion through the abdominal wall of a medical patient; insertion of the leading end into the vicinity of the peritoneal cavity of the patient; and introduction of both the first and second sensors through the axial lumen and into the vicinity of the peritoneal cavity.

The source of blue light may be structured and arranged to be implanted within the body of the patient. A direct current power supply may also be provided to excite the source of blue light through a layer of skin of the patient. In an alternative embodiment, the direct current power supply may be structured and arranged to be implanted within the body of the patient.

The photoreceptor may be structured and arranged to be implanted within the body of the patient. A processor may be provided to receive information signals from the photoreceptor through a layer of skin of the patient. In an alternative embodiment, the processor may be may be structured and arranged to be implanted within the body of the patient and to be in communication with a monitor for access to information from said processor. The processor may be placed in communication with a means of infusing insulin in accordance with a prescribed and preprogrammed insulin dosage, regimen, and protocol algorithm and responsive to information from the processor. The means of infusing insulin may be structured and arranged to comprise a reservoir implantable within the patient. The reservoir may be structured and arranged to be refillable.

A first sensor type may be characterized as being capable of measuring a variable, or a parameter, inside a body. A second sensor type may be characterized as being capable of measuring the same variable or parameter subsequent to a change being effected on that parameter, within a localized volume, by an agent. Such first and second sensors are desirably located in close proximity, but not so close that the first sensor is placed into the localized volume of altered chemistry. A physiological state, such as glucose level, can be inferred based upon a difference in the parameter as measured by the first and second sensor types. It is within contemplation for a sensing apparatus or device to include a plurality of such first and second sensors, arranged in a redundant array of sensors.

A desirable sensing apparatus is small enough to implant into a body using minimally invasive surgical techniques, such as by way of a catheter or cannula. A desirable outside diameter of an oxygen permeable housing for a sensing apparatus is up to about 3 mm, to facilitate placement of the sensing apparatus into the peritoneal cavity of a human patient using a catheter having a size of about 9 French. A sensing apparatus of such size can easily accommodate a plurality of fiber optic fibers, or some other sort of signal transmitting conduits, connected to a plurality of sensors of the first and second types. In one arrangement having optical fibers of about 100 micrometers in diameter, and in a sensing device having an outside diameter of about 3 mm, approximately 30 optical fibers can fit spaced along the device's diameter. Such a device may internally accommodate up to perhaps 100, or more redundant sensors of each of the first and second type. Sensors, such as optrodes having attached optical fibers, can be arranged and spaced apart in any workable and manufacturable arrangement along an axis of the device. One spacing arrangement has sensors of the first type arranged as a core around which are wrapped sensors of the second type, with an axial spacing provided between sensors of first and second types.

The plurality of redundant signals provided in such a multisensor device permits manipulation of acquired data to improve durability, accuracy, and effectiveness of the device. Data manipulation within contemplation can include: signal averaging of multiple signals from each sensor type, elimination of signals from failed or erratic sensors, and as feedback to determine absolute and relative sensor stability and drift. Statistical parameters may be applied to discriminate and reject signals having too high or low of values as being outliers, or being due to individual sensor failure.

BRIEF DESCRIPTION OF THE DRAWINGS

In the drawings, which illustrate what is currently regarded as the best mode for carrying out the invention.

DETAILED DESCRIPTION OF THE ILLUSTRATED EMBODIMENT

Figure 1:
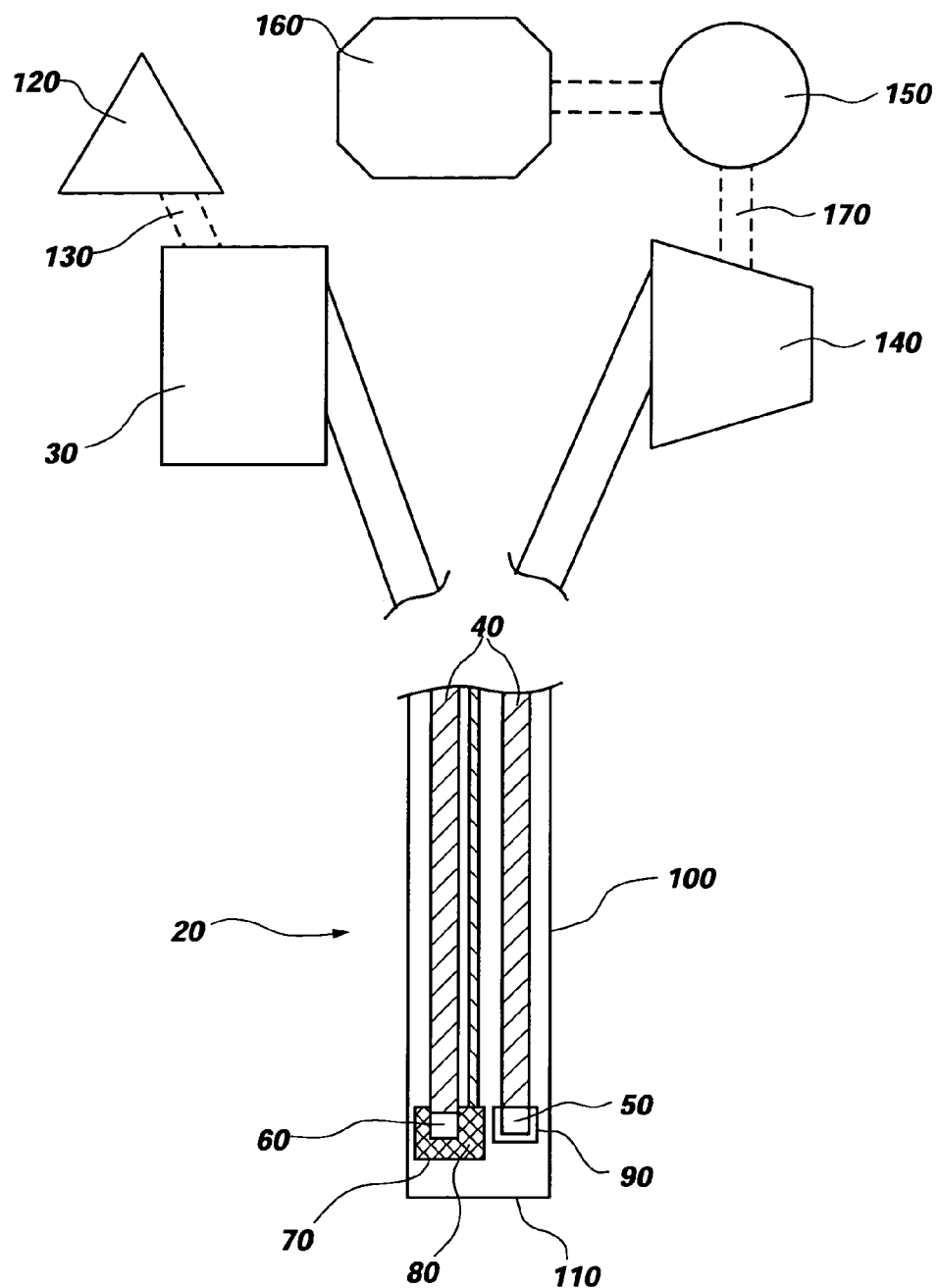
FIG. 1 is a partially exploded cross-sectional side view in elevation and diagram of the invention.

FIG. 1 illustrates a preferred embodiment in which an oxygen sensor probe, designated generally 20, comprises a conventional oxygen sensor probe. An example of such a probe 20, well established in the art, is available through Oceanoptics as a fiber optic oxygen sensor probe typically used to measure oxygen levels in water to monitor marine life activity. A light emitting diode ("LED") 30 source of blue light that generates an electromagnetic pulse or current of energy in the wavelength range of about 500 nanometers or less is associated with an optical fiber, or a plurality or bundle of optical fibers or fiber assembly 40, which conveys the blue light energy to the probe 20.

First 50 and second 60 cooperating sensors within the probe 20 comprise a ruthenium II complex matrix which absorbs the blue light. The second 60 of the two sensors-60 further comprises a pocket 70 containing glucose oxidase 80. Each of the sensors is encapsulated by an oxygen permeable polymer barrier 90, typically comprising a type of silicone. The blue light, energy as it enters the sensors 50, 60 fluoresces and is reemitted as a red light wavelength in the range of about 600 nanometers or greater.

The two sensors 50, 60 provide disparate signals resulting from their respective interactions with ambient oxygen in the peritoneal cavity enabling a comparison from which glucose levels in the same vicinity are inferred. In the present invention, inferences from such signals are drawn essentially in real time due to placement of the probe 20 in the vicinity of the peritoneum, i.e., in proximity to the portal vein associated with the liver and kidneys, within which vein physiologically definitive glucose levels exist. Glucose levels in the peritoneal fluid closely approximate glucose levels in the blood within the portal vein with a reduced lag time as compared with glucose levels adduced from samples taken from extremities such as the arms, legs and interstitial fluid, even when taken from abdominal skin.

The source of the blue light, such as the LED 30, may be located subcutaneously. Alternatively, the LED source of the blue light 30 may be external to the body. If the LED is externally located, then the wavelength penetrability is enhanced at lower nanometer ranges near the less optimal ultraviolet ("UV") spectrum, provided a greater intensity is utilized, not only because the spectrum of light energy is UV but also because it may need to be conveyed transdermally.

Each fiber or fiber bundle 40 optimally comprises a diameter of at least 50 microns up to around 600 microns. As energy is transmitted along the fiber or fibers of fiber bundle 40, a greater loss of energy is experienced as the diameter is reduced. Disadvantageously, fiber diameters in excess of 600 microns or about ½ millimeter, though useable with the present invention, result in the need for a much larger incision at the site of fiber penetration into the patient's body.

A cannula or catheter 100 in the range of 14 to 24 gauge internal diameter, and which may be formed of a polymer material, is beneficially utilized to encase the fiber or fiber bundles 40 associated with the respective sensors 50, 60 encapsulated in the probe 20 at the distal probe end 110 of the fiber or fiber bundles 40.

The catheter 100 containing the fibers of fiber bundle 40 and sensors 50, 60 may be anchored by any conventional means, e.g., tissue suture and associated external catheter PIC line tab externally anchored with tape (not shown). While it is contemplated that many of the various components of the system, apparatus and method of the present invention may be implanted in the vicinity of the peritoneal cavity, in the embodiment illustrated in FIG. 1 the catheter 100 encasing the fibers or fiber bundles 40 is situated percutaneously to associate the probe 20 with, for example, the LED 30 and other electronic elements of the invention.

A direct current ("DC") power supply 120 at a proximal fiber end 130 of the fiber or fibers of fiber bundle 40 may be utilized to excite the LED 30. In percutaneous configurations the DC power supply 120 is located externally. However, the present invention alternatively contemplates location of the DC power supply 120 internal the medical patient in some embodiments.

A photoreceptor 140, e.g., a photo diode or photo cell, is structured and arranged to receive information from the two sensors 50, 60 and to forward the information to a central processing unit ("CPU") 150 for comparison of the information from the first sensor 50 with the information from the second sensor 60. As with the DC power supply 120, the photoreceptor 140 may be located internally or externally and thus associated with the probe 20 percutaneously, but it is contemplated that in some configurations of the present invention the photoreceptor 140 could be located internal the patient in some embodiments, one of which is depicted in FIG. 2, elaborated below.

The CPU 150 may be structured and arranged to give an output upon which a user may base a decision of how much insulin to inject. Alternatively, the CPU 150 may be structured and arranged to provide output formatted to enable automatic injection in accordance with, and in response to, a prescribed glucose level control algorithm. In a configuration in which a transdermally renewable, internally located reservoir of insulin 160 is associated with the present system and method, it will be appreciated that a self-contained, long-term, minimally invasive treatment of diabetes is contemplated.

In accordance with the foregoing, in configurations in which the LED 30 but not the DC power source 120 is indwelling, the LED 30 may be excited across the skin of the medical patient by a suitable transponder. Where the photoreceptor 140 is indwelling, an appropriately arranged transceiver 170 may receive and advance the signal as needed. Thus it may be recognized that any of a number of permutations of locations of the various components of the present system, apparatus and method would be within the ambit of the contemplated invention.

Figure 2:
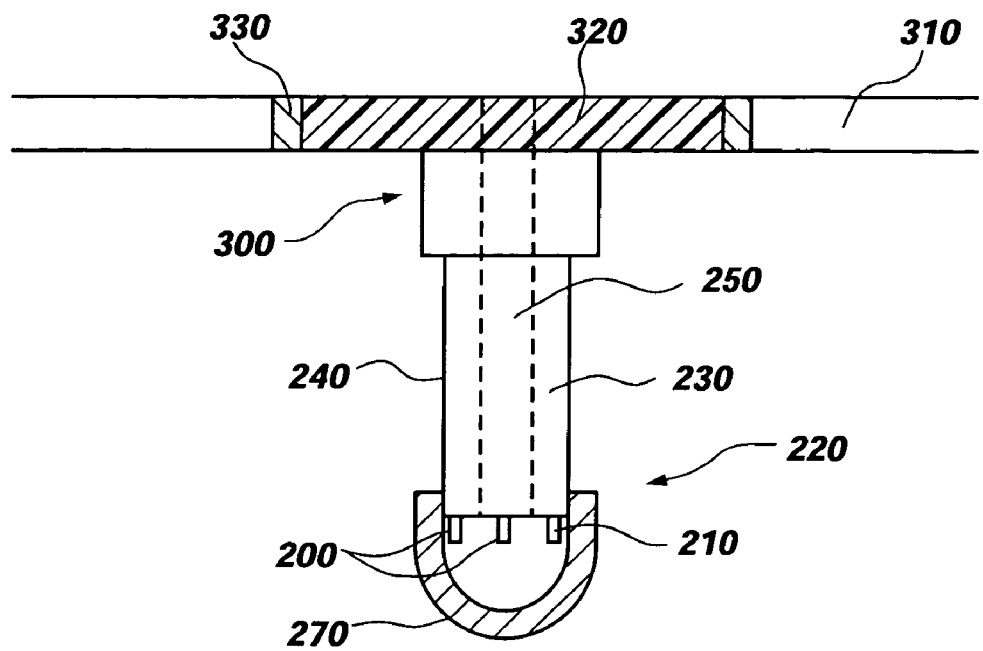
FIG. 2 is a cross-sectional side view of one configuration of the invention.
Figure 3:
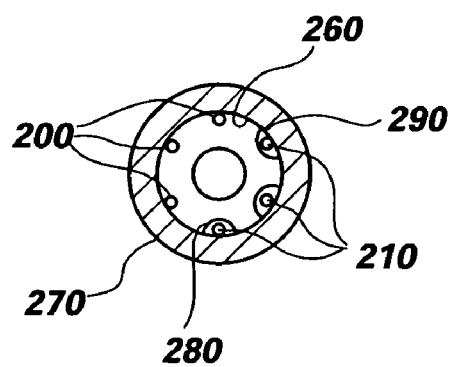
FIG. 3 is a bottom cross-sectional view in elevation of the sensor of the invention.

In FIGS. 2 and 3, the basic structural elements of a configuration of the presently preferred embodiment of the invention are set forth in which many of the primary components are located internally. The sensors 200, 210 are situated at the distal end 220 of a fiber assembly 230 within an encasing catheter or cannula 240. Additionally a flush tube 250 is enclosed with the fiber assembly 230. The flush tube 250 is in fluid communication with the glucose oxidase pocket 260 surrounding selected electrode sensors 200, 210. The pocket 260 is defined in part by a cap 270 and the catheter or cannula 240. The cap 270 comprises a filter fluid interface including potential breaches 280 which in response to increased pressure within the pocket 260 allow spent glucose oxidase mixture 290 to be flushed out upon selective periodic infusion of fresh glucose oxidase mixture.

The fiber assembly 230 as illustrated is associated with electronics, generally 300, for data transmission, storage, processing and the like. Though it is not necessary that such electronics be located beneath the skin 310, in the configuration depicted in FIGS. 2 and 3, the DC power supply, LED, photoreceptor or CPU or any or all such electronics 300 are characterized as being subdural. A silicone button 320 traverses an opening in the skin 310 and is structured and arranged to accommodate skin growth into and throughout periphery 330 of the silicone button 320. The flush tube 250 may be accessed through the silicone button 320 by introduction of a cannula such as a hypodermic needle (not shown) to introduce or exchange fluids essential to proper function of the system. It is contemplated that insulin and other therapeutic or palliative medicaments and the like may be introduced through the silicone button 320 and flush tube 250 and beyond the cap 270 to the medical patient as appropriate.

The system, apparatus and method of the present invention, while directed generally to the monitoring of glucose levels in the vicinity of the peritoneum in the context of diabetes should not be misunderstood to be limited to such monitoring. Many other physiological analytes susceptible to measurement may also be monitored by the present invention with few, minor modifications. An incomplete list of many such physiological analytes is as follows: Acetaminophen, Alpha Fetoprotein, Cancer Antigen 125, Estradiol, Folate, Progesterone, Prolactin, Triiodothyronine, Amphetamine and methamphetamine, Ethanol, Prostate Specific Antigen, Vitamin B-12, Carcinoembryonic Antigen (CAE), Follicle Stimulating Hormone (FSH), Luteinizing Hormone (LH), Procainamide, Procainamide Napa, Barbiturates, Gentamicin, Calicylate, Tobramycin, Benzodiazepines, Methadone, Phenytoin, Quinidine, Beta hCG, Cocaine, Thyroid Stimulating Hormone (hTSHII), Theophylline-II, Vancomycine-II, Opiate, Carbamezepine, Ferritin, Tricyclic Antidepressant, Thyroxine Total (T4), CK-MB, Troponin I, Digoxin, Phenobarbital, Thyroxine Free FT4, Vaiproic Acid, Rubella IgG, Myoglobin and Chemistry Critical Values Retire.

Additional substances susceptible to measurement under the present invention would include: Alanine Aminotransferase AL:T, Albumin, Alcohol, Alkaline Phophatase, Ammonia, Amylase, Aspartate Aminotransferase AST, Bicarbonate (ECO2), Bilirubin Bu Bc Tbil, Calcium, Carbamazepine, Chloride, Cholesterol, CKMB, C-Reactive Protein CRP, Creatine Kinase, Creatinine, Gamma Glutamyl Transferase GGT, Glucose (+CSF), High Density Lipoprotein HDLC, Iron, Lactate, Lactate Dehydrogenase LDH, Lipase, Lithium, Magnesium, Phenyloin, Phosphorus, Potassium, Protein (CSF), Calicylate, Sodium, Theophylline, Total Iron Binding Capacity TIBC, Total Protein, Triglycerides, Urea Nitrogen (BUN), Uric Acid, Urine Protein, Requesting Water Silicate Level, Albumin Excretion Rate, Fetal Fibronectin, Free Thyroxine (FTe)(IMx)w/TP & CT, Thyroid Stimulating Hormone (hTSHII), Homocystein (IMx) w/TP & CT and Tacromilus (FK506) (IMx).

The system, apparatus and method of the present invention provide distinct advantages over prior glucose monitoring paradigms. Thus, reference herein to specific details of the illustrated or other preferred embodiments is by way of example and is not intended to limit the scope of the appended claims. It will be apparent to those skilled in the art that many modifications of the basic illustrated embodiments may be made without departing from the spirit and scope of the invention as recited by the claims.

What is claimed is:

1. A method of measuring glucose concentration, comprising:

providing a first sensor wherein luminescent material encapsulated by a first oxygen permeable polymer barrier is located proximal a distal end of a first optical fiber;

providing a second sensor wherein luminescent material and glucose oxidase adjacent each other and together encapsulated by a second oxygen permeable polymer barrier are located proximal a distal end of a second optical fiber in near proximity to said first sensor for placement of said first and second sensors in the vicinity of a peritoneal cavity of a medical patient;

providing a catheter, comprising at least one auxiliary catheter lumen in communication with each said luminescent material, whereby said luminescent material upon becoming degraded through repeated fluorescing may be replaced with upgraded or new luminescent material;

providing a source of blue light, emissions of which transmitted through said distal ends of said first and second optical fibers are capable of fluorescing within said luminescent material of both said first and second sensors and of being reemitted in a form of red light from both said first and second sensors;

providing a photoreceptor structured and arranged to receive said reemitted red light from both said first and second sensors, said photoreceptor being in communication with a processor capable of comparing information transmitted through said photoreceptor from said first and second sensors;

providing a cannula, comprising an axial lumen and a leading end susceptible to insertion through an abdominal wall of said patient;

inserting said leading end into said vicinity of said peritoneal cavity of said patient;

introducing both said first and second sensors through said axial lumen and into said vicinity of said peritoneal cavity;

measuring glucose concentration with said first and second sensors; and displaying said measured glucose concentration.

2. The method according to claim 1, further comprising providing a direct current power supply which is located external said medical patient and which is structured and arranged to be capable of exciting said source of blue light.

3. The method according to claim 2, wherein said photoreceptor is located-external said patient.

4. The method according to claim 2, wherein said source of blue light and said photoreceptor are located external said patient.

5. The method according to claim 1, wherein said cannula upon insertion is structured and arranged to be capable of separating tissues comprising said abdominal wall with minimal severance of said tissues.

6. The method according to claim 1, wherein said first and second sensors are replaced periodically.

7. The method of claim 1, further comprising provision of a catheter assembly whereby therapeutic fluids may be infused into the vicinity of said peritoneal cavity.

8. The method of claim 7, wherein said catheter assembly comprises an in-line filter.

9. The method of claim 8, wherein said catheter assembly may be structured and arranged for disconnection of a proximal portion of said catheter assembly at a location proximal said filter in preparation for attachment of successive replacement catheter proximal portions.

10. The method according to claim 9, wherein said filter is structured and arranged to filter both air and impurities, including particulate matter and microorganisms harmful to said peritoneal cavity.

11. The method according to claim 9, whereby said therapeutic fluids are infused in response to direction from said processor based upon said information.

12. The method according to claim 11, wherein said therapeutic fluids are infused mechanically.

13. The method according to claim 12, wherein said mechanical infusion is automatic.

14. The method according to claim 12, wherein said mechanical infusion is remotely actuated.

15. The method according to claim 11, wherein said therapeutic fluids are infused manually.

16. A method of measuring glucose concentration, comprising:

providing a first sensor wherein luminescent material encapsulated by a first oxygen permeable polymer barrier is located proximal a distal end of a first optical fiber;

providing a second sensor wherein luminescent material and glucose oxidase adjacent each other and together encapsulated by a second oxygen permeable polymer barrier are located proximal a distal end of a second optical fiber in near proximity to said first sensor for placement of said first and second sensors in vicinity of a peritoneal cavity of a medical patient;

providing a source of blue light, emissions of which transmitted through said distal ends of said first and second optical fibers are capable of fluorescing within said luminescent material of both said first and second sensors and of being reemitted in a form of red light from both said first and second sensors;

providing a photoreceptor structured and arranged to receive said reemitted red light from both said first and second sensors, said photoreceptor being in communication with a processor capable of comparing information transmitted through said photoreceptor from said first and second sensors;

providing a catheter, comprising an auxiliary lumen structured and arranged to be capable of being placed in communication with said glucose oxidase, said glucose oxidase configured for replacement with upgraded or new glucose oxidase upon becoming degraded from exposure to oxygen and glucose in said vicinity of said peritoneal cavity;

providing a cannula, comprising an axial lumen and a leading end susceptible to insertion through an abdominal wall of said patient;

inserting said leading end into said vicinity of said peritoneal cavity of said patient;

introducing both said first and second sensors through said axial lumen and into said vicinity of said peritoneal cavity;

measuring glucose concentration with said first and second sensors; and displaying said measured glucose concentration.

17. The method according to claim 16, wherein said source of blue light is structured and arranged to be implanted within a body of said patient.

18. The method according to claim 17, wherein a direct current power supply is provided to excite said source of blue light through a layer of skin of said patient.

19. The method according to claim 17, wherein a direct current power supply is provided to excite said source of blue light and is structured and arranged to be implanted within said body of said patient.

20. The method according to claim 16, wherein said photoreceptor is structured and arranged to be implanted internal said patient.

21. The method according to claim 20, wherein a processor is provided to receive information signals from said photoreceptor through a layer of skin of said patient.

22. The method according to claim 21, wherein said processor is placed in communication with a means of infusing insulin in accordance with a prescribed and preprogrammed insulin dosage, regimen, and protocol algorithm and responsive to information from said processor.

23. The method according to claim 22, wherein said means of infusing insulin is structured and arranged to comprise a reservoir implantable within said patient.

24. The method according to claim 23, wherein said reservoir is structured and arranged to be refillable.

25. The method according to claim 20, wherein a processor is provided to receive information signals from said photoreceptor and is structured and arranged to be implanted internal said patient and to be in communication with a monitor for access to information from said processor.

26. A system for measuring glucose concentration, comprising:

a first sensor wherein luminescent material encapsulated by a first oxygen permeable polymer barrier is located proximal a distal end of a first optical fiber;

a second sensor wherein luminescent material and glucose oxidase adjacent each other and together encapsulated by a second oxygen permeable polymer barrier are located proximal a distal end of a second optical fiber in near proximity to said first sensor for placement of said first and second sensors in the vicinity of a peritoneal cavity of a medical patient, said first and second sensors configured to measure glucose concentration and operably coupled to a display configured for displaying said measured glucose concentration;

a catheter, comprising an auxiliary lumen structured and arranged to be capable of being placed in communication with said glucose oxidase, said glucose oxidase configured for replacement with upgraded or new glucose oxidase upon becoming degraded from exposure to oxygen and glucose in said vicinity of said peritoneal cavity;

a source of blue light, emissions of which transmitted through said distal ends of said first and second optical fibers are capable of fluorescing within said luminescent material of both said first and second sensors and of being reemitted in a form of red light from both said first and second sensors;

a photoreceptor structured and arranged to receive said reemitted red light from both said first and second sensors, said photoreceptor being in communication with a processor capable of comparing information transmitted through said photoreceptor from said first and second sensors; and a cannula, comprising an axial lumen and a leading end susceptible to insertion through an abdominal wall of said patient.

27. The system according to claim 26, wherein said blue light comprises electromagnetic wavelengths less than 500 nanometers.

28. The system according to claim 26, wherein said red light comprises electromagnetic wavelengths in excess of 600 nanometers.

29. The system according to claim 26, wherein said first and second optical fibers each have a diameter between about 50 micrometers and about 600 micrometers.

30. The system according to claim 26 wherein said luminescent material comprises ruthenium (II) complex or an aromatic hydrocarbon.

31. The system according to claim 30, wherein said aromatic hydrocarbon includes carbazole, acridone, fluoranthene, 9,10-diphenylanthracene, phrysene, benz(a)anthracene, tetracene, pyrene, dibenz(ah)anthracene, perylene, benzo(ghi)perylene, coronene, anthanthrene, decacyclene, 1-aminoanthracene, 2-aminoanthracene or 1-aminopyrene.

32. A system for measuring glucose concentration, comprising:

a first sensor wherein luminescent material encapsulated by a first oxygen permeable polymer barrier is located proximal a distal end of a first optical fiber;

a second sensor wherein luminescent material and glucose oxidase adjacent each other and together encapsulated by a second oxygen permeable polymer barrier are located proximal a distal end of a second optical fiber in near proximity to said first sensor for placement of said first and second sensors in the vicinity of a peritoneal cavity of a medical patient, said first and second sensors configured to measure glucose concentration and operably coupled to a display configured for displaying said measured glucose concentration;

a catheter, comprising at least one auxiliary catheter lumen in communication with said luminescent material, said luminescent material configured for replacement with upgraded or new luminescent material upon becoming degraded through repeated fluorescing;

a source of blue light, emissions of which transmitted through said distal ends of said first and second optical fibers are capable of fluorescing within said luminescent material of both said first and second sensors and of being reemitted in a form of red light from both said first and second sensors;

a photoreceptor structured and arranged to receive said reemitted red light from both said first and second sensors, said photoreceptor being in communication with a processor capable of comparing information transmitted through said photoreceptor from said first and second sensors; and a cannula, comprising an axial lumen and a leading end susceptible to insertion through an abdominal wall of said patient.

33. The system according to claim 32, further comprising a direct current power supply which is configured to be located outside a body of said patient and which is structured and arranged to excite said source of blue light.

34. The system according to claim 33, wherein said photoreceptor is located outside of said body.

35. The system according to claim 34, wherein said source of blue light and said photoreceptor is located outside of said body.

36. The system according to claim 32, wherein said cannula is configured to separate with minimal severance of bodily tissues surrounding said peritoneal cavity upon insertion of said cannula through said tissues, whereby a passage is opened for placement of said first and second sensors within said peritoneal cavity.

* * * * *